(12) United States Patent
Xu et al.

(10) Patent No.: US 10,653,746 B2
(45) Date of Patent: May 19, 2020

(54) MEDICAMENT FOR USE IN TREATING GOUT

(71) Applicant: Baozhen Xu, Weifang, Shandong (CN)

(72) Inventors: Baozhen Xu, Weifang (CN); Qian Cheng, Weifang (CN); Long Cheng, Weifang (CN)

(73) Assignee: Baozhen Xu, Shandong (CN)

( * ) Notice: Subject to any disclaimer, the term of this patent is extended or adjusted under 35 U.S.C. 154(b) by 0 days.

(21) Appl. No.: 16/074,011

(22) PCT Filed: Jan. 20, 2017

(86) PCT No.: PCT/CN2017/071864
§ 371 (c)(1),
(2) Date: Jul. 30, 2018

(87) PCT Pub. No.: WO2017/129058
PCT Pub. Date: Aug. 3, 2017

(65) Prior Publication Data
US 2019/0038706 A1  Feb. 7, 2019

(30) Foreign Application Priority Data
Jan. 29, 2016 (CN) .......................... 2016 1 0063691

(51) Int. Cl.
| | | |
|---|---|---|
| *A61K 38/16* | (2006.01) | |
| *A61P 19/06* | (2006.01) | |
| *A61K 31/7012* | (2006.01) | |
| *A61K 31/715* | (2006.01) | |
| *A61K 36/21* | (2006.01) | |
| *A61K 38/14* | (2006.01) | |
| *A61K 36/48* | (2006.01) | |
| *A61K 38/10* | (2006.01) | |
| *A61K 36/315* | (2006.01) | |
| *A61K 36/898* | (2006.01) | |
| *A61K 36/05* | (2006.01) | |

(52) U.S. Cl.
CPC .......... *A61K 38/16* (2013.01); *A61K 31/7012* (2013.01); *A61K 31/715* (2013.01); *A61K 36/21* (2013.01); *A61K 36/315* (2013.01); *A61K 36/48* (2013.01); *A61K 36/898* (2013.01); *A61K 38/10* (2013.01); *A61K 38/14* (2013.01); *A61P 19/06* (2018.01); *A61K 36/05* (2013.01)

(58) Field of Classification Search
CPC ..................................................... A61K 38/16
See application file for complete search history.

(56) References Cited

U.S. PATENT DOCUMENTS

| | | | |
|---|---|---|---|
| 2010/0048507 A1 | 2/2010 | Hisatome et al. | |
| 2013/0101514 A1* | 4/2013 | Cushing ............... | A61K 31/201 424/9.1 |
| 2015/0306054 A1 | 10/2015 | Selley | |
| 2015/0337001 A1 | 11/2015 | Kim et al. | |

FOREIGN PATENT DOCUMENTS

| | | | |
|---|---|---|---|
| CN | 1045586 A | | 9/1990 |
| CN | 101002873 A | | 7/2007 |
| CN | 101703710 A | * | 5/2010 |
| CN | 102077933 A | * | 6/2011 |
| CN | 102077933 A | | 6/2011 |
| CN | 103585561 A | | 2/2014 |

OTHER PUBLICATIONS

Chiovotti et al. Eur. J. Phycol., 38: 351-360. (Year: 2003).*
Go et al. "A glycoprotein from Laminaria japonica induces apoptosis in HT-29 colon cancer cells." Toxicology in Vitro, 2010, vol. 24, pp. 1546-1553.
Apr. 21, 2017 International Search Report issued in International Patent Application No. PCT/CN2017/071864.

* cited by examiner

Primary Examiner — Amy L Clark
(74) Attorney, Agent, or Firm — Oliff PLC

(57) ABSTRACT

A medicament for use in treating gout, the medicament being a glycoprotein, a mixture of polysaccharide and protein, a polypeptide or a protein.

1 Claim, No Drawings

MEDICAMENT FOR USE IN TREATING GOUT

TECHNICAL FIELD

The present invention relates to a medicament for use in treating gout, and belongs to the technical field of medical technology.

BACKGROUND TECHNOLOGY

Gout is a disease caused by a disorder of purine metabolism. Its clinical manifestations are characteristic acute arthritis, gophus formation, and gouty chronic arthritis caused by hyperuricemia and urate crystal deposition, patients may experience urate nephropathy and uric acid-related urinary calculus; in severe cases, patients may experience joint disability and renal insufficiency. The prerequisite for the onset of gout is hyperuricemia. Therefore, hyperuricemia is the most important biochemical basis for gout, followed by inflammatory response caused by urate deposition. With the improvement of people's living standards, the incidence of hyperuricemia and primary gout has been increasing on a year-to-year basis due to the changes in dietary structure, especially the increase in alcohol, especially beer, as well as the decrease in physical activity; the age of onset is increasingly younger. Since the uric acid is supersaturated in the blood, in addition to direct damage to bones and joints, it will also deposit in the kidneys, causing kidney disease, which poses a greater risk to human health and has drawn widespread attention in the medical community.

At present, western medicine treats hyperuricemia and gout by stages. Western medicine usually uses non-steroidal anti-inflammatory drugs (such as etoricoxib, celecoxib), uric acid-lowering drugs (such as allopurinol, febuxostat, probenecid and benzbromarone), glucocorticoids and colchicine etc, during the acute phase; as for the treatments during the intermittent and chronic stages, patients are often treated with diet control and uric-acid-lowering drugs; although non-steroidal anti-inflammatory drugs can quickly control the polar attack of gout, the drug only exerts an analgesic role during the onset stage of gout, but a relieve in pain does not cure the disease, the treatment only focuses on the relieving of symptoms and ignores the elimination of cause root, and these drugs have serious toxicity.

Patent: *ASTER GLEHNI* EXTRACTS, FRACTIONS OR COMPOUNDS ISOLATED THEREFROM FOR THE TREATMENT OR PREVENTION OF HYPERURICEMIA OR GOUT Patent Number is US2015337001 (A1), it is disclosed that: the invention relates to an *aster glehni* extract capable of preventing and improving hyperuricemia or gout, with the effect of inhibiting uric acid production and reducing its concentration.

Patent: THE USE OF BUCILLAMINE IN THE TREATMENT OF GOUT, Patent No. US20153060.54 (A1), it is disclosed that: disclosed are pharmaceutical compositions comprising, bucillamine, including bucillamine and allopurinol or colchicine, or pharmaceutically acceptable salts or solvates thereof, together with one or more pharmaceutically acceptable carriers, diluents and excipients. It is disclosed that methods for use of the said compositions in the treatment of gout and metabolic syndrome are also disclosed.

Patent: a traditional Chinese medicine composition for treating gout, Patent No. CN201310601617.4, it is disclosed that:

A traditional Chinese medicine composition for treating gout relates to a traditional Chinese medicine composition. The invention aims to solve the problem that the western medicine has many side effects on the human body in gout treatment and the treatment only focuses on the relieving of symptoms and ignores the elimination of cause root. The traditional Chinese medicine composition for treating gout hereof comprises, by weight, 5-10 portions of *Sophora flavescens,* 10-15 portions of *epimedium,* 5-10 portions of prepared *aconite* root, 4-8 portions of *ligusticum wallichii,* 8-12 portions of *pyrrosia lingua,* 6-9 parts of papaya and 3-6 portions of fructus *amomi*. The traditional Chinese medicine composition for treating gout has small side effects on the human body, and is capable of relieving the symptoms and eliminating cause root, with a overall clinical response rate of 96.7%. The invention is used for the treatment of gout.

The mechanism of action of traditional Chinese medicine for treating gout is complicated, and the clinical efficacy remains unclear. At present, there is no clinically recommended Chinese patent medicine for treating gout, and domestic gout patients western practically reline for western medicine for treatment.

Content of Invention

The present invention provides a medicament for use in treating gout in order to solve the deficiencies in the prior art for the purpose to achieve the following objectives hereof:

(1) The medicament hereof has the characteristics of high efficiency, safety and no side effects, and has good therapeutic effect on human gout, with a total effective rate of 98% and a low recurrence rate.

(2) The medicament hereof reduces the content of urine protein in gout rats model;

(3) The medicament hereof reduces the content of creatinine in gout rats model;

(4) The medicament hereof reduces the content of usea nitrogen in gout rats model;

(5) The medicament hereof reduces the content of blood uric acid in hyperuricemia mice model.

In Order to Solve the Aforesaid Problems, the Present Invention Adopts the Following Technical Solution:

A medicament for use in treating gout, characterized in that the medicament is a glycoprotein, or a mixture of polysaccharide and protein, or a polypeptide, or a protein; the glycoproteins comprises, by weight content, 1-99% sugar and 1-99% protein; the mixture of polysaccharide and protein comprises, by weight content, 1-99% sugar and 1-99% protein. The molecular weight of the glycoprotein is 0.2 to 3000 kDa.

The following are further modifications to the above technical solution:

The medicament is a marine algal glycoprotein.

The marine algal glycoprotein comprises, by weight content, 1-99% sugar and 1-99% protein; the mixture of marine algal polysaccharide and protein, by weight content, 1-99% polysaccharide and 1-99% protein.

The marine algal glycoprotein has a molecular weight of 0.2-3000 kDa; as for the mixture of polysaccharide and protein, a molecular weight of the polysaccharide is 0.2-3000 kDa, and a molecular weight of the protein is 0.2-3000 kDa.

The said medicament comprises, by weight content, 1-99 portions of glycoprotein and 1-25 portions of glucuronic acid.

The said medicament comprises, by weight content, 1-99 portions of marine algal glycoprotein and 1-25 portions of glucuronic acid.

The said medicament comprises, by weight content, 1-99 portions of marine algal glycoprotein and 1-25 portions of glucuronic acid, 2-9 portions of indigo naturalis.

The algae comprises one or more kinds of blue-green algae, green algae, red algae, gold algae, and brown algae.

The said medicament comprises, by weight content, 1-99 portions of marine algal glycoprotein, 8-14 portions of indigo naturalis, and 7-13 portions of twotooth *achyranthes* root.

The said medicament comprises, by weight content, 1-99 portions of marine algal glycoprotein, 8-14 portions of indigo naturalis, 7-13 portions of twotooth *achyranthes* root and 1-15 portions of glucuronic acid.

The said medicament comprises, by weight content, 1-99% sugar and 1-99% protein.

The said marine algal glycoprotein comprises, by weight content, 1-99% sugar and 1-99% protein.

Compared with the Prior Art, the Avantages of the Present Invention are:

(1) The medicament hereof has significant therapeutic effect on human gout, with a total effective rate of 98%, of which the rate of well-healed is 85%, the rate of marked efficacy is 13% and the rate of inefficacy is only 2%. As for the healed patients, the recurrence rate in 5 years is only 1%;

(2) The medicament hereof reduces the content of urine protein in gout rats model; after four weeks administration of the gout rats model, the urine protein value of the rat is 50.89-16838 mg/L; the urine protein value of the rat in the model control group is 364.83 mg/L;

(3) The medicament hereof reduces the content of creatinine in gout model; after four weeks administration of gout rats model, the creatinine value of the rat is 152.45-172.82 mg/L; the creatinine value of the rat in the model control group is 288.01 mmol/L;

(4) The medicament hereof reduces the content of usea nitrogen in gout rats model; after four weeks administration of gout rats model, the urea nitrogen value of the rat is 11.58-15.64 mmol/L; the urea nitrogen value in the model control group is 56.07 mmol/L;

(5) The medicament hereof reduces the content of blood uric acid in hyperuricemia mice model; the mice administered with the medicament in the invention has a blood uric acid value of 147.89-160.5 μmol/L; the mice in the model control group has a blood uric acid value of 250.4 μmol/L.

SPECIFIC EMBODIMENTS

The preferred embodiments of the present invention are described in the following, and the preferred embodiments described herein are only intended to illustrate and explain the invention, but not limited to this invention.

Embodiment 1 A Medicament for Use in Treating Gout

Wherein the medicament is a marine algal glycoprotein;
The marine algal glycoprotein comprises, by weight content, 1% sugar and 99% protein;
The molecular weight is 0.2 kDa;
The said sugar is a polysaccharide;
The said marine algae is blue-green algae;
The said polysaccharide comprises: glucose, galactose, mannose and rhamnose;
The said protein comprises: arginine, lysine, serine, and threonine.

Embodiment 2 A Medicament for Use in Treating Gout

Wherein the medicament is a marine algal glycoprotein;
The marine algal glycoprotein comprises, by weight content, 9% sugar and 88% protein;
The molecular weight is 3 kDa;
The said sugar is a polysaccharide;
The said marine algae is blue-green algae;
The said polysaccharide comprises: glucose, galactose, mannose and rhamnose;
The said protein comprises: arginine, lysine, serine, and threonine.

Embodiment 3 A Medicament for Use in Treating Gout

Wherein the medicament is a marine algal glycoprotein;
The marine algal glycoprotein comprises, by weight content, 16% sugar and 80% protein;
The molecular weight is 25 kDa;
The said sugar is a polysaccharide;
The said marine algae is chlorella;
The said polysaccharide comprises: glucose, galactose, mannose and rhamnose;
The said protein comprises: arginine, lysine, serine, and threonine.

Embodiment 4 A Medicament for Use in Treating Gout

Wherein the medicament is a marine algal glycoprotein;
The marine algal glycoprotein comprises, by weight content, 30% sugar and 70% protein;
The molecular weight is 40 kDa;
The said sugar is a polysaccharide;
The said marine algae is red algae;
The said polysaccharide comprises: glucose, galactose, mannose and rhamnose;
The said protein comprises: arginine, lysine, serine, and threonine.

Embodiment 5 A Medicament for Use in Treating Gout

Wherein the medicament is a marine algal glycoprotein;
The marine algal glycoprotein comprises, by weight content, 50% sugar and 50% protein;
The molecular weight is 100 kDa;
The said sugar is a polysaccharide;
The said marine algae is brown algae;
The said polysaccharide comprises: glucose, galactose, mannose and rhamnose;
The said protein comprises: arginine, lysine, serine, and threonine.

Embodiment 6 A Medicament for Use in Treating Gout

Wherein the medicament is a marine algal glycoprotein;
The marine algal glycoprotein comprises, by weight content, 99% sugar and 1% protein;
The molecular weight is 3000 kDa;
The said sugar is a polysaccharide;
The said marine algae is gold algae;
The said polysaccharide comprises: glucose, galactose, mannose and rhamnose;

The said protein comprises: arginine, lysine, serine, and threonine.

The glycoprotein said in these above embodiments 1-6 further includes a pigment; the said pigment is a natural pigment contained in algal substances;

These above embodiments 1-6 could be summarized as:

A Medicament for use in Treating Gout

The said medicament is a glycoprotein;

The glycoprotein comprises, by weight content, 1-99% sugar and 1-99% protein;

The molecular weight is 0.2-30000 kDa;

The said sugar is a polysaccharide;

The said medicament includes synthetic glycoproteins and synthetic polysaccharides and proteins.

The said protein comprises 20 kinds of amino acids and 8 kinds of synthetic amino acids; The preparation method of the said medicament: the glycoprotein is prepared into capsules and tablets etc. according to a conventional process; the mixture of the polysaccharide and the protein is prepared into capsules and tablets etc. according to a conventional process.

Embodiment 7 Application of the Said Medicament in Treating Gout (1) Therapeutic Effect of the Medicament in the Present Invention on Gout Rats Model Induced by Streptozotocin In model control groups and the invention groups, the streptozotocin was first used to induce gout in rats, and then the rats in the invention groups were administered the medicament prepared by the present invention and administered intragastrically three times a day; the rats in control group were administered the distilled water, and the value of urine protein, and the creatinine and urea nitrogen content were measured four weeks later, with the results shown in Table 1 and Table 2.

(2) Therapeutic Effect of the Medicament in the Present Invention on Hyperuricemia Mice Model Induced by Xanthine A. Experimental Materials Animals: 50 clean-grade Kunming mice, male, 20 g±2 g Medicament: the medicament described in Embodiments 1-6

Xanthine: Sinopharm Chemical Reagent Co., Ltd., batch number of WL20101109

Blood uric acid test kit: Shanghai Rongsheng Biotech Co., Ltd., batch number of 20100406

B. Experimental Method

Mice were randomly divided into 8 groups after entering the laboratory, namely normal control group, model control group, and present invention groups 1-6, 10 rats in each group, weighed and numbered;

After one-week adaptive feeding, the mice in the normal control group and the model control group were administered distilled water by means of intragastric administration, and mice 1-6 in the invention group were administered the medicament in the present invention at a dose of 3 g/day, administered intragastrically, three times a day for three consecutive days.

At one hour after the last intragastric administration, the mice in normal control group were intraperitoneally injected with normal saline 0.1 mL/1.0 g, and the mice in the other 7 groups were intraperitoneally injected with 10% xanthine suspension 0.1 mL/10 g for modeling. Ater 0.5 h, the blood was taken by eyeball removal method, the uric acid value was measured and the measurement results were statistically analyzed. The experimental results are shown in Table 3.

TABLE 1

Effect of the medicament in the present invention on gout rats model induced by streptozotocin

| Group | Dose (g/day) | Urine protein(mg/L) | Creatinine(mmol/L) | Usea nitrogen(mmol/L) |
|---|---|---|---|---|
| Normal control group |  |  | 133.39 ± 13.91 | 6.37 ± 2.48 |
| Model control group |  | 364.83 ± 20.62 | 288.01 ± 12.35 | 56.07 ± 3.00 |
| Embodiment 1 | 3 | 110.43 ± 21.32 | 169.65 ± 10.05 | 14.67 ± 2.30 |
| Embodiment 2 | 3 | 50.89 ± 22.14 | 152.45 ± 10.89 | 11.58 ± 2.60 |
| Embodiment 3 | 3 | 62.13 ± 23.96 | 158.48 ± 13.59 | 12.12 ± 3.29 |
| Embodiment 4 | 3 | 107.45 ± 22.76 | 162.23 ± 10.67 | 13.75 ± 2.50 |
| Embodiment 5 | 3 | 130.12 ± 21.23 | 166.18 ± 11.25 | 14.41 ± 3.30 |
| Embodiment 6 | 3 | 168.78 ± 22.70 | 172.82 ± 11.10 | 15.64 ± 2.93 |

Embodiments 2 and 3 are preferred embodiments.

TABLE 2

Effect of the medicament in the present invention at different doses on gout rats model induced by streptozotocin

| Group | Dose (g/day) | Urine protein(mg/L) | Creatinine(mmol/L) | Usea nitrogen(mmol/L) |
|---|---|---|---|---|
| Normal control group | — | — | 133.39 ± 13.91 | 6.37 ± 2.48 |
| Model control group | — | 364.83 ± 20.62 | 288.01 ± 12.35 | 56.07 ± 3.00 |
| Embodiment 2 | 0.4 | 80.12 ± 20.23 | 178.22 ± 11.15 | 15.24 ± 2.63 |
| Embodiment 2 | 0.8 | 65.45 ± 22.26 | 162.38 ± 13.19 | 12.28 ± 2.29 |
| Embodiment 2 | 3 | 50.89 ± 22.14 | 152.45 ± 10.89 | 11.58 ± 2.60 |
| Embodiment 2 | 4 | 70.22 ± 21.25 | 155.12 ± 11.20 | 12.64 ± 2.33 |
| Embodiment 2 | 6 | 92.32 ± 22.34 | 162.48 ± 12.19 | 13.12 ± 2.59 |
| Embodiment 2 | 8 | 108.25 ± 20.89 | 179.82 ± 10.32 | 14.64 ± 2.41 |

TABLE 3

Effect of the medicament in the present invention on blood uric acid in hyperuricemia mice model

| Group | Dose (g/day) | Blood Uric acid(μmol/L) |
|---|---|---|
| Normal control group | — | 126.4 ± 15.48 |
| Model control group | — | 250.4 ± 17.62 |
| Embodiment 1 | 3 | 160.13 ± 16.96 |
| Embodiment 2 | 3 | 147.89 ± 18.14 |
| Embodiment 3 | 3 | 150.43 ± 18.32 |
| Embodiment 4 | 3 | 153.45 ± 17.76 |
| Embodiment 5 | 3 | 158.12 ± 18.23 |
| Embodiment 6 | 3 | 160.5 ± 16.70 |

Embodiments 2 and 3 are preferred embodiments.

TABLE 4

Effect of the medicament in the present invention at different doses on blood uric acid in hyperuricemia mice model

| Group | Dose (g/day) | Blood Uric acid(μmol/L) |
|---|---|---|
| Normal control group | — | 126.4 ± 15.48 |
| Model control group | — | 250.4 ± 17.62 |
| Embodiment 2 | 0.4 | 175.5 ± 15.80 |
| Embodiment 2 | 0.8 | 150.13 ± 16.36 |
| Embodiment 2 | 3 | 147.89 ± 17.84 |
| Embodiment 2 | 4 | 152.12 ± 18.03 |
| Embodiment 2 | 6 | 157.45 ± 17.46 |
| Embodiment 2 | 8 | 172.89 ± 17.25 |

(3) Human Clinical Trials

The human clinical trials are as follows:

A total of 100 cases were included, 52 males and 48 females, aged from 32 years old to 61 years old, with a course of disease ranging from 6 months to 8 years, mostly 3 to 5 years; as the first metatarsophalangeal joint swelling and pain, 50 cases had the unilateral involvement and 50 cases had the bilateral involvement; wherein 60 cases of unilateral arthritis, 40 cases of pain and inflammation involving bilateral joints, and wherein 10 cases of the presence of arthritic calculus. All cases passed the examination and all the 100 cases had an increase in blood uric acid. For all of them, the possibility of being caused by medications or other diseases was ruled out.

Treatment Methods:

All the gout-treating medicament in Embodiment 3 were administered 3 g per day, in 3 times, 3 times per day, to be taken after being mixed with warm boiled water. 21 days remained a course of treatment, usually a course of treatment was needed, and the efficacy was observed at the end of the treatment. Efficacy assessment criteria Healing: all clinical symptoms disappeared, joints could move freely, the blood uric acid decreased to a value within the normal range; marked efficacy: clinical symptoms improved, joint activity was flexible, and the blood uric acid decreased by more than 10%; no response: no change in symptoms and laboratory test indicators.

Results:

Healed: 85 cases, accounting for 85%;

Marked efficacy: 13 cases, accounting for 13%;

No response: 2 cases, accounting for 2%;

Total effective rate: 98%;

The recurrence rate is low, and as for the healed patients, the recurrence rate in 5 years is only 1%.

Embodiment 8 A Medicament for Use in Treating Gout

It Comprises, on the Basis of Weight, the Following Components:

1 portion of marine algal glycoprotein and 1 portion of glucuronic acid;

The marine algal glycoprotein comprises, by weight content, 9% sugar and 88% protein;

The molecular weight is 8 kDa;

The said sugar is a polysaccharide;

The said marine algae is spirulina;

The said polysaccharide comprises: glucose, galactose, mannose and rhamnose;

The said protein comprises: arginine, lysine, serine, and threonine.

Embodiment 9 A Medicament for Use in Treating Gout

It comprises, on the Basis of Weight, the Following Components:

15 portions of marine algal glycoprotein and 6 portions of glucuronic acid;

The marine algal glycoprotein comprises, by weight content, 9% sugar and 88% protein;

The molecular weight is 12 kDa;

The said sugar is a polysaccharide;

The said marine algae is chlorella;

The said polysaccharide comprises: glucose, galactose, mannose and rhamnose;

The said protein comprises: arginine, lysine, serine, and threonine.

Embodiment 10 A Medicament for Use in Treating Gout

It Comprises, on the Basis of Weight, the Following Components:

40 portions of marine algal glycoprotein and 13 portions of glucuronic acid;

The marine algal glycoprotein comprises, by weight content, 30% sugar and 70% protein;

The molecular weight is 20 kDa;

The said sugar is a polysaccharide;

The said marine algae is *Bangiaatropurpurea*(Roth) C. Agardh;

The said polysaccharide comprises: glucose, galactose, mannose and rhamnose;

The said protein comprises: arginine, lysine, serine, and threonine.

Embodiment 11 A Medicament for Use in Treating Gout

It Comprises, on the Basis of Weight, the Following Components;

70 portions of marine algal glycoprotein and 17 portions of glucuronic acid;

The marine algal glycoprotein comprises, by weight content, 50% sugar and 50% protein;

The molecular weight is 8 kDa;

The said sugar is a polysaccharide;

The said marine algae is gulfweed;

The said polysaccharide comprises: glucose, galactose, mannose and rhamnose;

The said protein comprises: arginine, lysine, serine, and threonine.

Embodiment 12 A Medicament for Use in Treating Gout

It Comprises, on the Basis of Weight, the Following Components:
99 portions of marine algal glycoprotein and 25 portions of glucuronic acid;
The marine algal glycoprotein comprises, by weight content, 99% sugar and 1% protein;
The molecular weight is 20 kDa;
The said sugar is a polysaccharide;
The said marine algae is synuraceae urelin;
The said polysaccharide comprises: glucose, galactose, mannose and rhamnose;
The said protein comprises: arginine, lysine, serine, and threonine.

Embodiment 13 A Medicament for Use in Treating Gout

It Comprises, on the Basis of Weight, the Following Components:
1 portion of marine algal glycoprotein, 1 portion of glucuronic acid and 2 portions of indigo naturalis;
The marine algal glycoprotein comprises, by weight content, 9% sugar and 88% protein;
The molecular weight is 6 kDa;
The said sugar is a polysaccharide;
The said marine algae is blue-green algae;
The said polysaccharide comprises: glucose, galactose, mannose and rhamnose;
The said protein comprises: arginine, lysine, serine, and threonine.

Embodiment 14 A Medicament for Use in Treating Gout

It Comprises, on the Basis of Weight, the Following Components:
27 portions of marine algal glycoprotein, 6 portions of glucuronic acid and 4 portions of indigo naturalis;
The marine algal glycoprotein comprises, by weight content, 9% sugar and 88% protein;
The molecular weight is 20 kDa;
The said sugar is a polysaccharide;
The said marine algae is blue-green algae;
The said polysaccharide comprises: glucose, galactose, mannose and rhamnose;
The said protein comprises: arginine, lysine, serine, and threonine.

Embodiment 15 A Medicament for Use in Treating Gout

It Comprises, on the Basis of Weight, the Following Components:
52 portions of marine algal glycoprotein, 14 portions of glucuronic acid and 5 portions of indigo naturalis;
The marine algal glycoprotein comprises, by weight content 30% sugar and 70% protein;
The molecular weight is 200 kDa;
The said sugar is a polysaccharide;
The said marine algae is blue-green algae;
The said polysaccharide comprises: glucose, galactose, mannose and rhamnose;
The said protein comprises: arginine, lysine, serine, and threonine.

Embodiment 16 A Medicament for Use in Treating Gout

It Comprises, on the Basis of Weight, the Following Components:
99 portions of marine algal glycoprotein, 25 portions of glucuronic acid and 9 portions of indigo naturalis;
The marine algal glycoprotein comprises, by weight content, 50% sugar and 50% protein;
The molecular weight is 3000 kDa;
The said sugar is a polysaccharide;
The said marine algae is blue-green algae;
The said polysaccharide comprises: glucose, galactose, mannose and rhamnose;
The said protein comprises: arginine, serine, and threonine.

Application of the said Medicament in Embodiment 8-Embodiment 16 in Treating Gout Using the test method said in Embodiment 7, the medicament said in Embodiment 8-Embodiment 16 in this invention groups have the following application effects:

(1) Effects of the Medicament in the Present Invention on Gout Rats Model Induced by Streptozotocin

TABLE 5

Effects of the medicament in the present invention on gout rats model induced by streptozotocin

| Group | Dose (g/day) | Urine protein(mg/L) | Creatinine(mmol/L) | Usea nitrogen(mmol/L) |
| --- | --- | --- | --- | --- |
| Normal control group | — | — | 130.39 ± 13.91 | 6.57 ± 2.48 |
| Model control group | — | 364.83 ± 20.62 | 288.01 ± 12.35 | 56.07 ± 3.00 |
| Embodiment 8 | 3 | 48.89 ± 20.14 | 150.15 ± 10.29 | 10.20 ± 2.50 |
| Embodiment 9 | 3 | 48.60 ± 20.02 | 149.80 ± 10.14 | 10.00 ± 2.23 |
| Embodiment 10 | 3 | 30.5 ± 19.54 | 135.56 ± 10.28 | 7.89 ± 1.95 |
| Embodiment 11 | 3 | 48.50 ± 19.82 | 149.45 ± 10.21 | 9.94 ± 2.20 |
| Embodiment 12 | 3 | 48.60 ± 19.24 | 149.25 ± 10.18 | 9.92 ± 2.14 |
| Embodiment 13 | 3 | 47.65 ± 19.75 | 148.15 ± 10.00 | 9.90 ± 1.98 |
| Embodiment 14 | 3 | 47.29 ± 19.85 | 150.15 ± 9.90 | 9.95 ± 2.00 |
| Embodiment 15 | 3 | 32.24 ± 19.56 | 136.15 ± 10.16 | 7.70 ± 1.96 |
| Embodiment 16 | 3 | 47.59 ± 19.47 | 150.15 ± 10.27 | 9.89 ± 1.95 |

(2) Therapeutic Effect of the Medicament in the Present Invention on Hyperuricemia Mice Model Induced by Xanthine

TABLE 6

Effect of the medicament in the present invention on hyperuricemia mice model

| Group | Dose (g/day) | Blood Uric acid(μmol/L) |
|---|---|---|
| Normal control group | — | 127.4 ± 15.48 |
| Model control group | — | 250.4 ± 17.62 |
| Embodiment 8 | 3 | 146.21 ± 17.54 |
| Embodiment 9 | 3 | 145.01 ± 17.37 |
| Embodiment 10 | 3 | 135.25 ± 17.08 |
| Embodiment 11 | 3 | 145.21 ± 17.44 |
| Embodiment 12 | 3 | 146.04 ± 17.21 |
| Embodiment 13 | 3 | 146.11 ± 16.95 |
| Embodiment 14 | 3 | 146.00 ± 17.08 |
| Embodiment 15 | 3 | 134.34 ± 17.12 |
| Embodiment 16 | 3 | 146.24 ± 17.04 |

(3) Human Clinical Trials

Results:

Healed: 88 cases, accounting for 88%;

Marked efficacy: 10 cases, accounting for 10%;

No response: 2 cases, accounting for 2%;

Total effective rate: 98%;

The recurrence rate is low, and as for the healed patients, the recurrence rate in 6 years is only 1%.

Embodiment 17 A Medicament for Use in Treating Gout

It Comprises, on the Basis of Weight, the Following Components:

1 portion of marine algal glycoprotein, 8 portions of indigo naturalis, and 7 portions of twotooth *achyranthes* root;

The marine algal glycoprotein comprises, by weight content, 10% sugar and 85% protein;

The molecular weight is 16 kDa;

The said sugar is a polysaccharide;

The said marine algae is spirulina;

The said polysaccharide comprises: glucose, galactose, mannose and rhamnose;

The said protein comprises: arginine, lysine, serine, and threonine.

Embodiment 18 A Medicament for Use in Treating Gout

It Comprises, on the Basis of Weight, the Following Components:

40 portions of marine algal glycoprotein, 11 portions of indigo naturalis, and 9 portions of twotooth *achyranthes* root;

The marine algal glycoprotein comprises, by weight content, 8% sugar and 88% protein;

The molecular weight is 14 kDa;

The said sugar is a polysaccharide;

The said marine algae is chlorella;

The said polysaccharide comprises: glucose, galactose, mannose and rhamnose;

The said protein comprises: arginine, lysine, serine, and threonine.

Embodiment 19 A Medicament for Use in Treating Gout

It Comprises, on the Basis of Weight, the Following Components:

99 portions of marine algal glycoprotein, 14 portions of indigo naturalis, and 13 portions of twotooth *achyranthes* root;

The marine algal glycoprotein comprises, by weight content, 30% sugar and 70% protein;

The molecular weight is 38 kDa;

The said sugar is a polysaccharide;

The said marine algae is *Gelidium amansii* Lamx;

The said polysaccharide comprises: glucose, galactose, mannose and rhamnose;

The said protein comprises: arginine, lysine, serine, and threonine.

Embodiment 20 A Medicament for Use in Treating Gout

It Comprises, on the Basis of Weight, the Following Components:

1 portion of marine algal glycoprotein, 8 portions of indigo naturalis, 7 portions of twotooth *achyranthes* root and 1 portion of glucuronic acid;

The marine algal glycoprotein comprises, by weight content, 10% sugar and 85% protein;

The molecular weight is 16 kDa;

The said sugar is a polysaccharide;

The said marine algae is spirulina;

The said polysaccharide comprises: glucose, galactose, mannose and rhamnose;

The said protein comprises: arginine, lysine, serine, and threonine.

Embodiment 21 A Medicament for Use in Treating Gout

It Comprises, on the Basis of Weight, the Following Components:

40 portions of marine algal glycoprotein, 11 portions of indigo naturalis, 9 portions of twotooth *achyranthes* root and 8 glucuronic acid;

The marine algal glycoprotein comprises, by weight content, 8% sugar and 88% protein;

The molecular weight is 14 kDa;

The said sugar is a polysaccharide;

The said marine algae is chlorella;

The said polysaccharide comprises: glucose, galactose, mannose and rhamnose;

The said protein comprises: arginine, lysine, serine, and threonine.

Embodiment 22 A Medicament for Use in Treating Gout

It Comprises, on the Basis of Weight, the Following Components:

99 portions of marine algal glycoprotein, 14 portions of indigo naturalis, 13 portions of twotooth *achyranthes* root and 15 portions of glucuronic acid;

The marine algal glycoprotein comprises, by weight content, 30% sugar and 70% protein;

The molecular weight is 200 kDa;
The said sugar is a polysaccharide;
The said marine algae is Gelidium amansii Lamx;
The said polysaccharide comprises: glucose, galactose, mannose and rhamnose;
The said protein comprises: arginine, lysine, serine, and threonine.

Application of the said Medicament in Embodiment 17-Embodiment 22 in Treating Gout Using the test method said in Embodiment 7, the medicament said in Embodiment 17-Embodiment 22 in this invention groups have the following application effects:

(1) Effects of the Medicament in the Present Invention on Gout Rats Model Induced by Streptozotocin

TABLE 7

Effects of the medicament in the present invention on gout rats model induced by streptozotocin

| Group | Dose g/day | Urine protein(mg/L) | Creatinine(mmol/L) | Usea nitrogen(mmol/L) |
|---|---|---|---|---|
| Normal control group | — | — | 130.39 ± 13.91 | 6.57 ± 2.48 |
| Model control group | — | 364.83 ± 20.62 | 288.01 ± 12.35 | 56.07 ± 3.00 |
| Embodiment 17 | 3 | 46.60 ± 19.68 | 147.80 ± 10.00 | 9.80 ± 2.14 |
| Embodiment 18 | 3 | 28.7 ± 19.27 | 132.56 ± 10.02 | 6.69 ± 1.92 |
| Embodiment 19 | 3 | 46.24 ± 19.75 | 147.65 ± 9.97 | 9.84 ± 1.97 |
| Embodiment 20 | 3 | 45.45 ± 19.68 | 145.25 ± 10.05 | 9.70 ± 2.14 |
| Embodiment 21 | 3 | 27.5 ± 19.54 | 130.36 ± 10.28 | 6.64 ± 1.86 |
| Embodiment 22 | 3 | 45.30 ± 19.68 | 145.67 ± 10.19 | 9.74 ± 2.04 |

(2) Therapeutic effect of the Medicament in the Present Invention on Hyperuricemia Mice Model Induced by Xanthine

TABLE 8

Effect of the medicament in the present invention on hyperuricemia mice model

| Group | Dose (g/day) | Blood Uric acid(μmol/L) |
|---|---|---|
| Normal control group | — | 126.4 ± 15.48 |
| Model control group | — | 250.4 ± 17.62 |
| Embodiment 17 | 3 | 143.31 ± 17.57 |
| Embodiment 18 | 3 | 128.20 ± 17.42 |
| Embodiment 19 | 3 | 143.27 ± 17.35 |
| Embodiment 20 | 3 | 142.89 ± 17.05 |
| Embodiment 21 | 3 | 126.57 ± 17.18 |
| Embodiment 22 | 3 | 142.57 ± 17.17 |

(3) Human Clinical Trials
Results:
Healed: 90 cases, accounting for 90%;
Marked efficacy: 9 cases, accounting for 9%;
No response: 1 case, accounting for 1%;
Total effective rate: 99%;
The recurrence rate is low, and as for the healed patients, no recurrence was observed in 5 years.

Embodiment 23 A Medicament for Use in Treating Gout

It Comprises, on the Basis of Weight, the Following Components:

80 portions of marine algal glycoprotein, 10 portions of radix sophorae flavescentis, 5 portions of radices saussureae, 5 portions of rhododendron mariae, 7 portions of unispike kyllinga herb, 8 portions of fructus evodiae, 10 portions of pyrola herb;

The marine algal glycoprotein comprises, by weight content, 10% sugar and 85% protein;

The molecular weight is 15 kDa;

The said marine algae is green algae;

The said sugar, by weight, comprises the following components: 8 portions of glucose 5 portions of galactose, and 11 portions of carubinose;

The protein mentioned, by weight, includes the following components: 7 portions of serine, 9 portions of threonine, and 15 portions of hydroxylysine.

Embodiment 24 A Medicament for Use in Treating Gout

It Comprises, on the Basis of Weight, the Following Components:

75 portions of marine algal glycoprotein, 12 portions of epimedium, 8 portions of nutmeg, 7 portions of gallnut, 9 portions of radix aconiti lateralis preparata, 6 portions of gastrodia elata, and 5 portions of caulis sinomenii;

The marine algal glycoprotein comprises, by weight content, 12% sugar and 75% protein;

The molecular weight is 8 kDa;

The said marine algae is blue-green algae;

The said sugar, by weight, comprises the following components: 20 portions of glucose, 8 portions of galactose, and 15 portions of carubinose;

The protein mentioned, by weight, includes the following components: 10 portions of serine, 15 portions of threonine, and 17 portions of hydroxylysine.

Embodiment 25 A Medicament for Use in Treating Gout

It Comprises, on the basis of Weight, the Following Components:

70 portions of marine algal glycoprotein, 8 portions of monkshood, 6 portions of semen dolichoris, 5 portions of bombyx batryticatus, 3 portions of pinellia ternata, 7 portions of atractylodes rhizome, and 8 portions of pubescent angelica root;

The marine algal glycoprotein comprises, by weight content, 14% sugar and 72% protein;

The molecular weight is 20 kDa;

The said marine algae is blue-green algae;

The said sugar, by weight, comprises the following components: 20 portions of glucose, 8 portions of galactose, and 15 portions of carubinose;

The protein mentioned, by weight, includes the following components: 10 portions of serine, 15 portions of threonine, and 17 portions of hydroxylysine.

Embodiment 26 A Medicament for Use in Treating Gout

It Comprises, on the Basis of Weight, the Following Components:

78 portions of marine algal glycoprotein, 10 portions of *ligusticum wallichii*, 8 portions of *alismatis* rhizoma, 6 portions of *cimicifuga foetida*, 7 portions of glabrousleaf *pittosporum* leaf, 7 portions of *notoperygium* root, and 5 portions of Chinese *clematis* root;

The marine algal glycoprotein comprises, by weight content, 22% sugar and 69% protein;

The molecular weight is 100 kDa;

The said marine algae is blue-green algae;

The said sugar, by weight, comprises the following components: 20 portions of glucose, 8 portions of galactose, and 15 portions of carubinose;

The protein mentioned, by weight, includes the following components: 10 portions of serine, 15 portions of threonine, and 17 portions of hydroxylysine.

Embodiment 27 A Medicament for Use in Treating Gout

Step 1: Weighing

Weigh the marine algal glycoprotein and all Chinese medicine components according to the formula;

Step 2: Extraction of Chinese Medicine (1) Washing

Wash all Chinese medicine components with clear water, and remove the impurities;

(2) Crash and Microwave Extraction

The Chinese medicine is pulverized into 100-mesh medicinal material powder, 8 times of 50% ethanol is added, the temperature is controlled at 60° C., microwave radiation is performed at the microwave power of 260 W, microwave wavelength of 130 mm, a frequency of 1200 MHz for 5 min, then filtration is carried out, and finally the filtrate is collected;

The medicine dregs are separated, 6 times of clear water is added, the temperature is controlled at 50 □, microwave radiation is performed at the microwave power of 200 W, microwave wavelength of 140 mm, a frequency of 1250 MHz for 5 min, then filtration is carried out, and finally the filtrate is collected;

Pool the filtrate collected from the two procedures; atomize and dry to prepare them into Chinese medicine powder;

Step 3 Add Marine Algal Glycoprotein.

Mixing the powder of marine algal glycoprotein with the above prepared Chinese medicine powder to produce different dosage forms such as capsules, tablets and so on.

Application of the said Medicament in Embodiment 23-Embodiment 26 in Treating Gout Applying the test method specified in Embodiment 7, this invention group is the medicament mentioned in Embodiment 23-Embodiment 26, the applicable effects are as follows:

(1) Effects of the Medicament in the Present Invention on Gout Rats Model Induced by Streptozotocin

TABLE 9

Effects of the medicament in the present invention on gout rats model induced by streptozotocin

| Group | Dose (g/day) | Urine protein (mg/L) | Creatinine (mmol/L) | Usea nitrogen (mmol/L) |
|---|---|---|---|---|
| Normal control group | — | — | 130.39 ± 13.91 | 6.57 ± 2.48 |
| Model control group | — | 364.83 ± 20.62 | 288.01 ± 12.35 | 56.07 ± 3.00 |
| Embodiment 23 | 3 | 40.86 ± 20.02 | 130.25 ± 10.00 | 6.68 ± 2.25 |
| Embodiment 24 | 3 | 40.26 ± 20.12 | 130.15 ± 10.07 | 6.65 ± 2.15 |
| Embodiment 25 | 3 | 40.56 ± 20.25 | 131.23 ± 10.00 | 6.45 ± 2.34 |
| Embodiment 26 | 3 | 40.16 ± 20.35 | 130.05 ± 10.37 | 6.28 ± 2.25 |

(2) Therapeutic Effect of the Medicament in the Present Invention on Hyperuricemia Mice Model Induced by Xanthine

TABLE 10

Effect of the medicament in the present invention on hyperuricemia mice model

| Group | Dose (g/day) | Blood Uric acid (μmol/L) |
|---|---|---|
| Normal control group | — | 126.4 ± 15.48 |
| Model control group | — | 250.4 ± 17.62 |
| Embodiment 23 | 3 | 128.3 ± 12.25 |
| Embodiment 24 | 3 | 127.56 ± 12.35 |
| Embodiment 25 | 3 | 129.25 ± 12.24 |
| Embodiment 26 | 3 | 130.89 ± 12.19 |

(3) Human Clinical Trials

Results:

Healed: 90 cases, accounting for 90%;

Marked efficacy: 9 cases, accounting for 9%;

No response: 1 case, accounting for 1%;

Total effective rate: 99%;

The recurrence rate is low, and as for the healed patients, no recurrence was observed in 5 years.

For the medicament mentioned in this invention, pH is between 5.3-9.8, and 6.5-7.5 is preferred.

The invention has been subjected to a large number of experiments, and we have carried out multiple tests using a mixture of marine shells, bones of livestock and poultry, a mixture of glycoprotein, polysaccharides and proteins extracted from the skeleton of marine animals, and the objectives of the invention have also been achieved.

Embodiment 28 A Medicament for Use in Treating Gout

The said medicament is a mixture of polysaccharides and proteins;

The said medicament comprises, by weight content, 1-99% polysaccharide and 1-99% protein.

The said polysaccharide comprises: glucose, galactose, mannose and rhamnose;

The said protein comprises: arginine, lysine, serine, and threonine.

As for the said mixture of polysaccharide and the protein, the polysaccharide has a molecular weight of 0.2-3000 kDa and the protein has a molecular weight of 0.2-3000 kDa.

The mixture of polysaccharides and proteins, further a mixture of algal polysaccharides and algal proteins;

The said mixture of the algal polysaccharide and the algal protein also comprises a pigment;

The said pigment is a natural pigment contained in the algal substance;

The said algal protein may be phycocyanin, phycoerythrin or algae xanthoprotein.

The said glycoprotein includes synthetic glycoprotein, synthetic polysaccharide and protein, The medicament mentioned in this invention has a No Observed Adverse Effect Level (NOAEL) of 1.6 g/kg for 12-week oral administration for dogs, which is equivalent to 50 times the equivalent dose for humans, so it is concluded that the safety of the clinical trial can be guaranteed.

The medicament described in this invention can also be a health care product or a food.

The basic principles and main features of the present invention and the advantages of the present invention are shown and described above. It should be understood by the technicians in this field that, the present invention is not limited by the foregoing embodiments, and that what are described in the aforementioned embodiments and specification are only the principles of this invention; without departing from the spirit and scope of the invention, this invention may be subject to various changes and modifications, which will be included within the scope of the invention as claimed. The scope of the invention is defined by the appended claims and their equivalents.

The invention claimed is:

1. A medicament for use in treating gout comprising:
   78 parts by weight of a glycoprotein extracted from marine blue-green algae,
   10 parts by weight of *ligusticum* wallichii,
   8 parts by weight of *alismatis* rhizoma,
   6 parts by weight of *cimicifuga foetida,*
   7 parts by weight of glabrousleaf *pittosporum* leaf,
   7 parts by weight of *notoperygium* root, and
   5 parts by weight of Chinese *clematis* root.

* * * * *